(12) United States Patent  (10) Patent No.: US 9,289,145 B2
Grenz et al.  (45) Date of Patent: Mar. 22, 2016

(54) IDENTIFICATION OF ABNORMAL CARDIAC SUBSTRATE DURING LEFT-VENTRICULAR PACING

(71) Applicants: Medtronic, Inc., Minneapolis, MN (US); The United States of America as Represented by the Department of Veterans Affairs, Washington, DC (US)

(72) Inventors: Nathan A. Grenz, Shoreview, MN (US); Brett Atwater, Durham, NC (US); John F. Beshai, Scottsdale, AZ (US)

(73) Assignees: Medtronic, Inc., Minneapolis, MN (US); The United States of America as Represented by the Department of Veterans Affairs, Washington, DC (US)

( * ) Notice: Subject to any disclaimer, the term of this patent is extended or adjusted under 35 U.S.C. 154(b) by 103 days.

(21) Appl. No.: 14/098,252

(22) Filed: Dec. 5, 2013

(65) Prior Publication Data

US 2015/0157233 A1  Jun. 11, 2015

(51) Int. Cl.
*A61B 5/04* (2006.01)
*A61B 5/0452* (2006.01)
(Continued)

(52) U.S. Cl.
CPC ........... *A61B 5/04012* (2013.01); *A61B 5/0452* (2013.01); *A61B 18/12* (2013.01);
(Continued)

(58) Field of Classification Search
CPC ............................ A61B 5/0452; A61B 5/0456
USPC .................................................. 600/517, 510
See application file for complete search history.

(56) References Cited

U.S. PATENT DOCUMENTS 4,374,382 A 2/1983 Markowitz
4,682,603 A 7/1987 Franz
(Continued)

FOREIGN PATENT DOCUMENTS

WO 2009085457 A2 7/2009
WO 2012122517 A2 9/2012
WO 2012139116 A2 10/2012

OTHER PUBLICATIONS

Wrobleski et al., "Use of Electrogram Characteristics During Sinus Rhythm to Delineate the Endocardial Scar in a Porcine Model of Healed Myocardial Infarction," Journal of Cardiovascular Electrophysiology, vol. 14, No. 5, May 2003, pp. 524-529, Retrieved on Oct. 23, 2013 from http://onlinelibrary.wiley.com/doi/10.1046/j.1540-8167.2003.02499.x/abstract;jsessionid=6F02BD6ECB62E883316ACE473B5F13D0.f04t03?deniedAccessCustomisedMessage=&userIsAuthenticated=false (8 pages).
(Continued)

*Primary Examiner* — Amanda Patton
*Assistant Examiner* — Philip Edwards
(74) *Attorney, Agent, or Firm* — Shumaker & Sieffert, P.A.

(57) ABSTRACT

Techniques for identifying abnormal cardiac substrate, e.g., scar substrate, may be implemented, as an example, during implantation of a left-ventricular (LV) lead, e.g., for cardiac resynchronization therapy (CRT), which may enable placement of the LV lead to avoid the abnormal cardiac substrate. An example system for identifying abnormal cardiac substrate comprises at least one implantable LV lead comprising at least one bipolar electrode pair configured to sense a LV bipolar cardiac electrogram signal of LV tissue proximate the bipolar electrode pair. The system delivers cardiac pacing pulses to a left ventricle via at least one electrodes of the LV lead, which may be different then the electrodes of the bipolar pair, and which may be spaced at least a threshold distance from the bipolar pair of electrodes. The amplitude of paced depolarizations in the bipolar electrogram indicates whether tissue proximate the bipolar electrode pair comprises abnormal cardiac substrate.

27 Claims, 8 Drawing Sheets

(51) Int. Cl.
*A61B 18/12* (2006.01)
*A61N 1/37* (2006.01)
*A61N 1/368* (2006.01)
*A61N 1/05* (2006.01)

(52) U.S. Cl.
CPC ........... *A61N 1/3684* (2013.01); *A61N 1/3686* (2013.01); *A61N 1/3702* (2013.01); *A61N 1/056* (2013.01); *A61N 1/371* (2013.01)

(56) References Cited

U.S. PATENT DOCUMENTS

| | | | |
|---|---|---|---|
| 5,117,824 | A | 6/1992 | Keimel et al. |
| 5,545,186 | A | 8/1996 | Olson et al. |
| 5,755,736 | A | 5/1998 | Gillberg et al. |
| 6,066,094 | A | 5/2000 | Ben-Haim |
| 6,370,435 | B2 | 4/2002 | Panescu et al. |
| 6,725,085 | B2 | 4/2004 | Schwartzman et al. |
| 7,751,882 | B1 | 7/2010 | Helland |
| 7,769,436 | B1 | 8/2010 | Boileau et al. |
| 8,512,255 | B2 | 8/2013 | Scharf et al. |
| 2005/0149138 | A1 | 7/2005 | Min et al. |
| 2007/0049817 | A1 | 3/2007 | Preiss et al. |
| 2007/0073179 | A1* | 3/2007 | Afonso et al. ................. 600/523 |
| 2007/0197929 | A1 | 8/2007 | Porath et al. |
| 2007/0299351 | A1 | 12/2007 | Harlev et al. |
| 2008/0004667 | A1 | 1/2008 | Arcot-Krishnamurthy et al. |
| 2009/0006970 | A1 | 1/2009 | Jeffery et al. |
| 2009/0099468 | A1 | 4/2009 | Thiagalingam et al. |
| 2010/0113954 | A1 | 5/2010 | Zhou |
| 2011/0144510 | A1 | 6/2011 | Ryu et al. |
| 2011/0213260 | A1 | 9/2011 | Keel et al. |
| 2012/0203295 | A1 | 8/2012 | Maskara et al. |
| 2012/0290034 | A1 | 11/2012 | Rochat et al. |
| 2013/0006317 | A1 | 1/2013 | Keel et al. |
| 2013/0030314 | A1 | 1/2013 | Keel et al. |
| 2013/0116739 | A1 | 5/2013 | Brada et al. |
| 2013/0131527 | A1* | 5/2013 | Min et al. ....................... 600/510 |
| 2013/0218223 | A1 | 8/2013 | Ghosh et al. |

OTHER PUBLICATIONS

Verma et al., Short- and Long-Term Success of Substrate-Based Mapping and Ablation of Ventricular Tachycardia in Arrhythmogenic Right Ventricular Dysplasia, Circulation, 111:3209-3216 (2005), Retrieved on Oct. 23, 2013 from http://circ.ahajournals.org/content/111/24/3209.full (9 pages).

International Search Report and Written Opinion from International Application No. PCT/US20141068907, dated Feb. 18, 2015, 14 pp.

Response to Written Opinion dated Feb. 18, 2015, from International Application No. PCT/US2014/068907, filed on Oct. 2, 2015, 12 pp.

"Quartet: Left-Heart Lead," © 2011, retrieved from URL: www.cardion.cz/file/209/quartet-specsheet.pdf, 2 pp. (Applicant points out that, in accordance with MPEP 609.04(a), the 2011 year of copyright is sufficiently earlier than the effective U.S. filing date and any foriegn priority date of Dec. 5, 2013 so that the particular month of publication is not in issue.).

Second Written Opinion from International Application No. PCT/US2014/068907, dated Dec. 11, 2015, 8 pages.

Response to Second Written Opinion dated Dec. 11, 2015, from International Application No. PCT/US2014/068907, filed on Feb. 10, 2016, 5 pp.

* cited by examiner

IDENTIFICATION OF ABNORMAL CARDIAC SUBSTRATE DURING LEFT-VENTRICULAR PACING

This invention was created in the performance of a Cooperative Research and Development Agreement with the Department of Veterans Affairs, an agency of the U.S. Government, which has certain rights in this invention.

TECHNICAL FIELD

The disclosure relates to cardiac monitoring and therapy and, more particularly, to evaluation of cardiac tissue to determine a location for cardiac monitoring and therapy delivery.

BACKGROUND

Cardiac pacing is delivered to patients to treat a wide variety of cardiac dysfunctions. Cardiac pacing is often delivered by an implantable medical device (IMD), which may also provide cardioversion or defibrillation in response to detected cardiac tachyarrhythmias, if needed. The IMD delivers such stimulation to the heart via electrodes located on one or more leads, which are typically intracardiac leads.

Patients with heart failure may be treated with cardiac resynchronization therapy (CRT). CRT is a form of cardiac pacing. The ventricles of some heart failure patients contract in an uncoordinated, or asynchronous, manner, which greatly reduces the pumping efficiency of the ventricles. CRT delivers pacing pulses at particular times, e.g., atrio-ventircular (A-V) intervals and/or intra-ventricular (V-V) intervals, and particular locations, e.g., to one or both of the right and left ventricles, to re-coordinate the contraction of the ventricles. In some examples, CRT involves delivery of pacing pulses to both ventricles to synchronize their contraction. In other examples, CRT involves delivery of pacing pulses to one ventricle, such as the left ventricle, to synchronize its contraction with that of the right.

The effectiveness of CRT in improving a patient's cardiac function, referred to as CRT response, may be negatively affected when a left-ventricular (LV) pacing electrode is located proximate scar (or otherwise abnormal) substrate, e.g., because the abnormal substrate may not depolarize, and therefore not effectively propagate the depolarization throughout the left ventricle, in response to the pacing stimulus. Abnormal substrate may include epicardial and/or transmural scar substrate, as well as other abnormal substrate, such as fibrosis. During implantation, an LV lead may be repositioned to avoid abnormal substrate. Some LV leads include multiple electrodes available for selection for delivery of LV pacing, and may be referred to as multipolar leads. During or after implantation, a different electrode of a multipolar LV lead may be selected to avoid pacing via an electrode located proximate abnormal LV substrate.

One type of LV mapping procedure involves advancing a closely-spaced bipolar electrode pair at a distal end of a mapping catheter to a variety of LV locations, and determining the amplitude of ventricular depolarizations within the bipolar electrogram sensed by the bipolar electrode pair at the various LV locations. Amplitudes below a threshold are considered indicative of scar substrate at the location of the bipolar pair. Typically, the electrogram is sensed during intrinsic conduction, e.g., with ventricular activation via the His-Purkinje system during sinus rhythm, and the threshold is valid under these circumstances. Such an LV mapping procedure may be performed prior to LV lead implantation, or for patients with hemodynamically intolerable ventricular tachycardia, to identify scar substrate.

SUMMARY

In general, the disclosure is directed to devices, systems and techniques for identifying abnormal cardiac substrate, e.g., scar substrate, of the left ventricle during left-ventricular (LV) pacing. An LV lead implanted on the left ventricle, e.g., through the coronary sinus and into a cardiac vein on the left ventricle, includes a bipolar electrode pair to sense an LV bipolar cardiac electrogram signal of LV tissue proximate the bipolar electrode pair. Systems according to this disclosure may indicate whether the LV tissue proximate the bipolar electrode pair is abnormal cardiac substrate based on an amplitude, e.g., peak-to-peak amplitude, of LV-paced depolarizations within the LV bipolar cardiac electrogram signal. In some examples, another electrode (other than the electrodes of the bipolar pair) of the LV lead, or an electrode of another LV lead, delivers the LV pacing. The pacing electrode may be spaced at least a threshold distance from the bipolar pair of electrodes.

In one example, the disclosure is directed to a system for identifying abnormal cardiac substrate. The system comprises at least one implantable left-ventricular (LV) lead comprising a plurality of electrodes, wherein the plurality of electrodes includes at least one bipolar electrode pair configured to sense a LV bipolar cardiac electrogram signal of LV tissue proximate the bipolar electrode pair. The system further comprises a signal generator configured to deliver cardiac pacing pulses to a left ventricle via at least one of the plurality of electrodes of the at least one LV lead, and a cardiac tissue analysis module configured to determine an amplitude of a depolarization within the LV bipolar cardiac electrogram signal, the depolarization resulting from the delivery of cardiac pacing pulses to the left ventricle. The amplitude indicates whether the LV tissue proximate the bipolar electrode pair comprises abnormal cardiac substrate, and the cardiac tissue analysis module is further configured to provide an indication of whether the LV tissue proximate the bipolar electrode pair comprises abnormal cardiac substrate based on the amplitude.

In another example, the disclosure is directed to a method for identifying abnormal cardiac substrate comprising sensing, by a bipolar electrode pair, a left-ventricular (LV) bipolar cardiac electrogram signal of LV tissue proximate the bipolar electrode pair, wherein at least one implanted LV lead comprises a plurality of electrodes, and the plurality of electrodes includes the bipolar electrode pair. The method further comprises delivering, by a signal generator, cardiac pacing pulses to a left ventricle via at least one of the plurality of electrodes of the at least one LV lead, and determining, by a cardiac tissue analysis module, an amplitude of a depolarization within the LV bipolar cardiac electrogram signal, the depolarization resulting from the delivery of cardiac pacing pulses to the left ventricle. The amplitude indicates whether the LV tissue proximate the bipolar electrode pair comprises abnormal cardiac substrate. The method further comprises providing, by the cardiac tissue analysis module, an indication of whether the LV tissue proximate the bipolar electrode pair comprises abnormal cardiac substrate based on the amplitude.

In another example, the disclosure is directed to a system for identifying abnormal cardiac substrate. The system comprises means for sensing, via a bipolar electrode pair, a left-ventricular (LV) bipolar cardiac electrogram signal of LV tissue proximate the bipolar electrode pair, wherein at least one implantable LV lead comprises a plurality of electrodes, and the plurality of electrodes includes the bipolar electrode pair. The system further comprises means for delivering cardiac pacing pulses to a left ventricle via at least one of the plurality of electrodes of the at least one LV lead, and means for determining an amplitude of a depolarization within the LV bipolar cardiac electrogram signal, the depolarization resulting from the delivery of cardiac pacing pulses to the left ventricle. The amplitude indicates whether the LV tissue proximate the bipolar electrode pair comprises abnormal cardiac substrate, and the system further comprises means for providing an indication of whether the LV tissue proximate the bipolar electrode pair comprises abnormal cardiac substrate based on the amplitude.

In another example, the disclosure is directed to a non-transitory computer-readable storage medium comprising instructions that, when executed by at least one processor, cause the at least one processor to receive, via a bipolar electrode pair, a left-ventricular (LV) bipolar cardiac electrogram signal of LV tissue proximate the bipolar electrode pair, wherein at least one implantable LV lead comprises a plurality of electrodes, and the plurality of electrodes includes the bipolar electrode pair. The instructions further cause the processor to determine an amplitude of a depolarization within the LV bipolar cardiac electrogram signal, the depolarization resulting from the delivery of cardiac pacing pulses to a left ventricle via at least one of the plurality of electrodes of the at least one LV lead. The amplitude indicates whether the LV tissue proximate the bipolar electrode pair comprises abnormal cardiac substrate. The instructions further cause the processor to provide an indication of whether the LV tissue proximate the bipolar electrode pair comprises abnormal cardiac substrate based on the amplitude.

In another aspect, the disclosure is directed to a computer-readable storage medium, which may be an article of manufacture. The computer-readable storage medium includes computer-readable instructions for execution by one or more processors. The instructions cause one or more processors to perform any part of the techniques described herein. The instructions may be, for example, software instructions, such as those used to define a software or computer program. The software or computer program may be, for example, modified or otherwise updated base on a specific patient's requirements. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable storage medium is non-transitory.

The details of one or more examples consistent with the present disclosure are set forth in the accompanying drawings and the description below. Other features, objects, and advantages will be apparent from the description and drawings, and from the claims.

DETAILED DESCRIPTION

Figure 1:
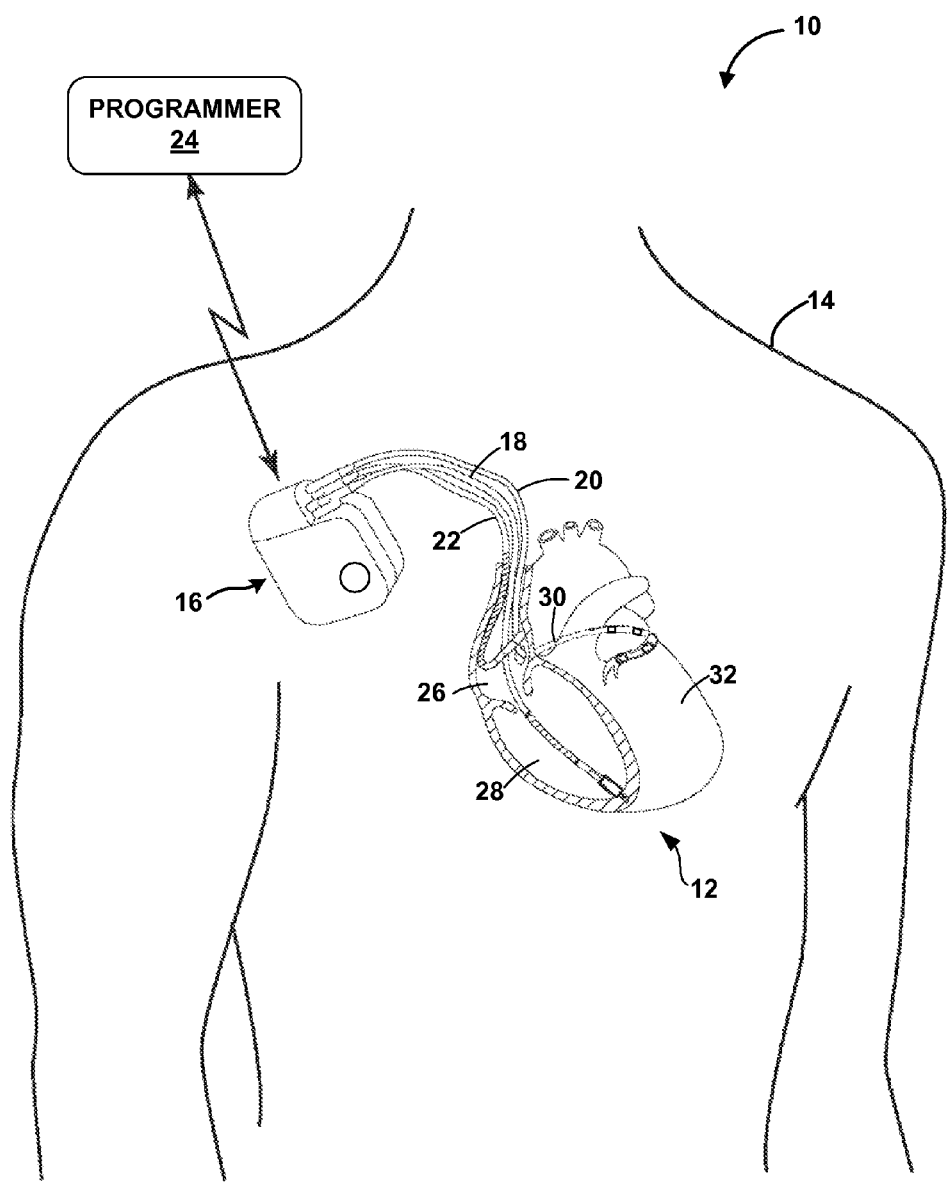
FIG. 1 is a conceptual diagram illustrating an example system for monitoring and treating cardiac events, which may be used to identify abnormal cardiac substrate according to the techniques of this disclosure.

This disclosure describes devices, systems and techniques for identifying abnormal cardiac substrate, e.g., scar substrate, of the left ventricle during left-ventricular (LV) pacing. An LV lead implanted on the left ventricle includes a bipolar electrode pair, e.g., a short-spaced sensing bipole, configured to sense an LV bipolar cardiac electrogram signal of LV tissue proximate the bipolar electrode pair. Systems according to this disclosure may indicate whether the LV tissue proximate the bipolar electrode pair is abnormal cardiac substrate based on an amplitude, e.g., peak-to-peak voltage, of LV-paced depolarizations within the LV bipolar cardiac electrogram signal. In some examples, another electrode (other than the electrodes of the bipolar pair) of the LV lead, or an electrode of another LV lead, delivers the LV pacing. In some examples, the pacing electrode is spaced at least a threshold distance from the bipolar pair of electrodes used to sense the LV bipolar cardiac electrogram.

As discussed above, some LV mapping procedures involve advancing a closely-spaced bipolar electrode pair at a distal end of a mapping catheter to a variety of LV locations, e.g., epicardially. Such mapping procedures may be performed to identify locations of scar substrate, or other abnormal cardiac substrate, based on the amplitudes of depolarizations sensed by the closely-spaced bipolar electrode pair. In general, a threshold depolarization amplitude may distinguish normal and abnormal cardiac substrate during such mapping procedures. Such LV mapping procedures may be performed in patients with hemodynamically intolerable ventricular tachycardia (VT) to identify abnormal substrate that may be causing or contributing to VT. Such LV mapping procedures may be performed, for example, prior to, or during, a cardiac ablation procedure to identify targets for ablation.

Such LV mapping procedures may also be performed prior to LV lead implantation. As discussed above, the effectiveness of CRT in improving a patient's cardiac function, referred to as CRT response, or the effectiveness of LV pacing in general, may be negatively affected when a left-ventricular (LV) pacing electrode is located proximate to scar (or otherwise abnormal) substrate. Accordingly, LV mapping procedures, using a mapping catheter that has a short-spaced sensing bipole, have been performed prior to LV lead implantation to identify abnormal substrate to avoid during LV lead implantation.

The mapping catheters used during such LV mapping procedures generally do not include additional electrodes for pacing. Accordingly, the electrogram is typically sensed by the closely-spaced bipole on the mapping catheter during intrinsic conduction. Furthermore, the depolarization amplitude threshold used to distinguish between normal and abnormal tissue during such procedures has been determined based on electrogram data collected from subjects during intrinsic conduction of sinus rhythm.

The techniques of this disclosure may facilitate identification of abnormal cardiac substrate during LV pacing. Identification of abnormal cardiac substrate during LV pacing may be desired in cases in which ventricular pacing is necessary because the patient has an underlying heart block. Identification of abnormal cardiac substrate during LV pacing may also be desired during implantation of an LV lead, e.g., during implantation of a system to deliver CRT. During implantation of an LV lead, e.g., for delivery of CRT, the lead may be implanted such that the distal portion of the lead is within the coronary sinus and/or a cardiac vein branching from the coronary sinus. The lead may be moved and/or different electrodes of the lead selected, to select different tissue sites of the LV for the delivery of the LV pacing. In some cases, cardiac performance metrics, such as cardiac output, or mechanical or electrical dyssynchrony, are monitored during delivery of LV pacing at different sites and/or with different timings relative to right-ventricular or atrial depolarization. A desired site and timing for LV pacing may be selected based on the cardiac performance metrics.

The disclosed techniques for identifying abnormal cardiac substrate may be implemented during implantation of an LV lead, e.g., for CRT, which may enable placement of the LV lead to avoid the abnormal cardiac substrate. Rather than using a separate mapping catheter to identify abnormal substrate, e.g., prior to implantation of the LV lead, the techniques of this disclosure may enable identification of abnormal cardiac substrate during implantation of the LV lead, by using a short-spaced bipolar pair of electrodes on the LV lead as a sensing bipole to identify the abnormal cardiac substrate. The LV lead may also deliver LV pacing during the identification of abnormal substrate, e.g., as described above for determining a stimulation site and timing for delivery of CRT. Delivery of the LV pacing through an electrode of the LV lead that is at least a threshold distance from the short-spaced bipolar pair of electrodes may enable, or increase the ability of, systems according to this disclosure to distinguish between normal and abnormal cardiac substrate during LV pacing.

The depolarization of the LV when paced is different than intrinsic depolarization of the LV. For example, paced depolarization of the LV may generally progress from epicardial to endocardial tissue, and from the pacing site, while intrinsic depolarization may generally progress from endocardial to epicardial tissue, and from the Purkinje fibers. Because the paced LV depolarization is different than intrinsic depolarization, the threshold depolarization amplitude for distinguishing between abnormal and normal cardiac substrate for catheter mapping procedures, during intrinsic sinus rhythm, may be inapplicable, or not as effective, for distinguishing between normal and abnormal cardiac substrate during LV pacing. Accordingly, techniques according to this disclosure may use a different threshold depolarization amplitude for distinguishing between abnormal and normal cardiac substrate, specific to LV pacing, compared to the threshold depolarization amplitude for distinguishing between abnormal and normal cardiac substrate for catheter mapping procedures.

FIG. 1 is a conceptual diagram illustrating an example system 10 for monitoring and treating cardiac events, which may be used to identify abnormal cardiac substrate according to the techniques of this disclosure. As illustrated by example system 10 in FIG. 1, a system for identifying abnormal cardiac substrate according to the techniques of this disclosure may include an IMD 16, such as an implantable cardiac pacemaker, implantable cardioverter/defibrillator (ICD), or pacemaker/cardioverter/defibrillator, for example. IMD 16 is connected to leads 18, 20 and 22 and is communicatively coupled to a programmer 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The therapy may be pacing, cardioversion and/or defibrillation pulses. IMD 16 may monitor EGM signals collected by electrodes on leads 18, 20 or 22, and based on the EGM signal, diagnose and treat cardiac episodes.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. A user may also interact with programmer 24 to program IMD 16, e.g., select values for operational parameters of the IMD. Programmer 24 may include a processor configured to evaluate EGM signals transmitted from IMD 16 to programmer 24.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

System 10 of FIG. 1 is an example of a system for identifying abnormal cardiac substrate according to the techniques of this disclosure. As will be described in greater detail below, LV lead 20 is an example of an implantable LV lead comprising a plurality of electrodes, wherein the plurality of electrodes includes at least one bipolar electrode pair configured to sense a LV bipolar cardiac electrogram signal of tissue of the left ventricle 32 of heart 12 proximate the bipolar electrode pair. In some examples, IMD 16 comprises a signal generator configured to deliver cardiac pacing pulses to left ventricle 32 of heart 12 via at least one of the plurality of electrodes of LV lead 20. The configuration of LV lead 20, such as the spacing between the electrodes of the bipolar pair, and the spacing between the pacing electrode and the electrodes of the bipolar pair, will be described in greater detail below.

In some examples, one or both of IMD 16 and programmer 24 includes a cardiac tissue analysis module configured to determine an amplitude of a depolarization within the LV bipolar cardiac electrogram signal, the depolarization resulting from the delivery of cardiac pacing pulses to left ventricle 32. As will be described in greater detail below, the amplitude indicates whether the LV tissue proximate the bipolar electrode pair comprises abnormal cardiac substrate. For example, the cardiac tissue analysis module may be configured to compare the amplitude to a threshold, where amplitude values below the threshold are indicative of abnormal cardiac substrate, such as scar substrate, and amplitudes above the threshold are indicative of normal cardiac substrate. The cardiac tissue analysis module is further configured to provide an indication of whether the LV tissue proximate the bipolar electrode pair comprises abnormal cardiac substrate based on the amplitude. In some examples, programmer 24, or another computing device, may include a user interface, and may provide an indication of whether the LV tissue proximate the bipolar electrode pair comprises abnormal cardiac substrate to a user, e.g., a surgeon, physician, or other clinician, via the user interface.

Although the techniques for identifying abnormal cardiac substrate according to the techniques of this disclosure are described herein primarily with reference to example system 10, the techniques may be performed by other systems that differ from example system 10. For example, systems for identifying abnormal cardiac substrate according to the techniques of this disclosure may include an IMD having different functionality than IMD 16, and may include more, fewer or different implantable cardiac leads than leads 18, 20 and 22. In some examples, systems for identifying abnormal cardiac substrate according to the techniques of this disclosure may include only one LV lead 20, or one or more LV leads. Additionally, systems for identifying abnormal cardiac substrate according to the techniques of this disclosure need not include programmer 24. In some examples, systems for identifying abnormal cardiac substrate according to the techniques of this disclosure may include any external computing device capable of communicating with an IMD according to the techniques of this disclosure, and need not include other functionality, e.g., for programming IMD, attributed to programmer 24 herein.

Additionally, some example systems for identifying abnormal cardiac substrate according to the techniques of this disclosure need not include either IMD 16 or programmer 24. In some examples, while implanted on left ventricle 32, e.g., during an LV lead implantation procedure, LV lead 20 may be coupled to an external device capable of providing functionality attributed to IMD 16 and programmer 24 herein, such as an external pacemaker analyzer. In such example, the external device may comprise a signal generator configured to deliver cardiac pacing pulses to left ventricle 32 of heart 12 via at least one of the plurality of electrodes of LV lead 20, as well as a cardiac tissue analysis module as described herein. Additionally, external device may comprise a user interface, and may provide an indication of whether the LV tissue proximate the bipolar electrode pair comprises abnormal cardiac substrate to a user via the user interface.

Figure 2:
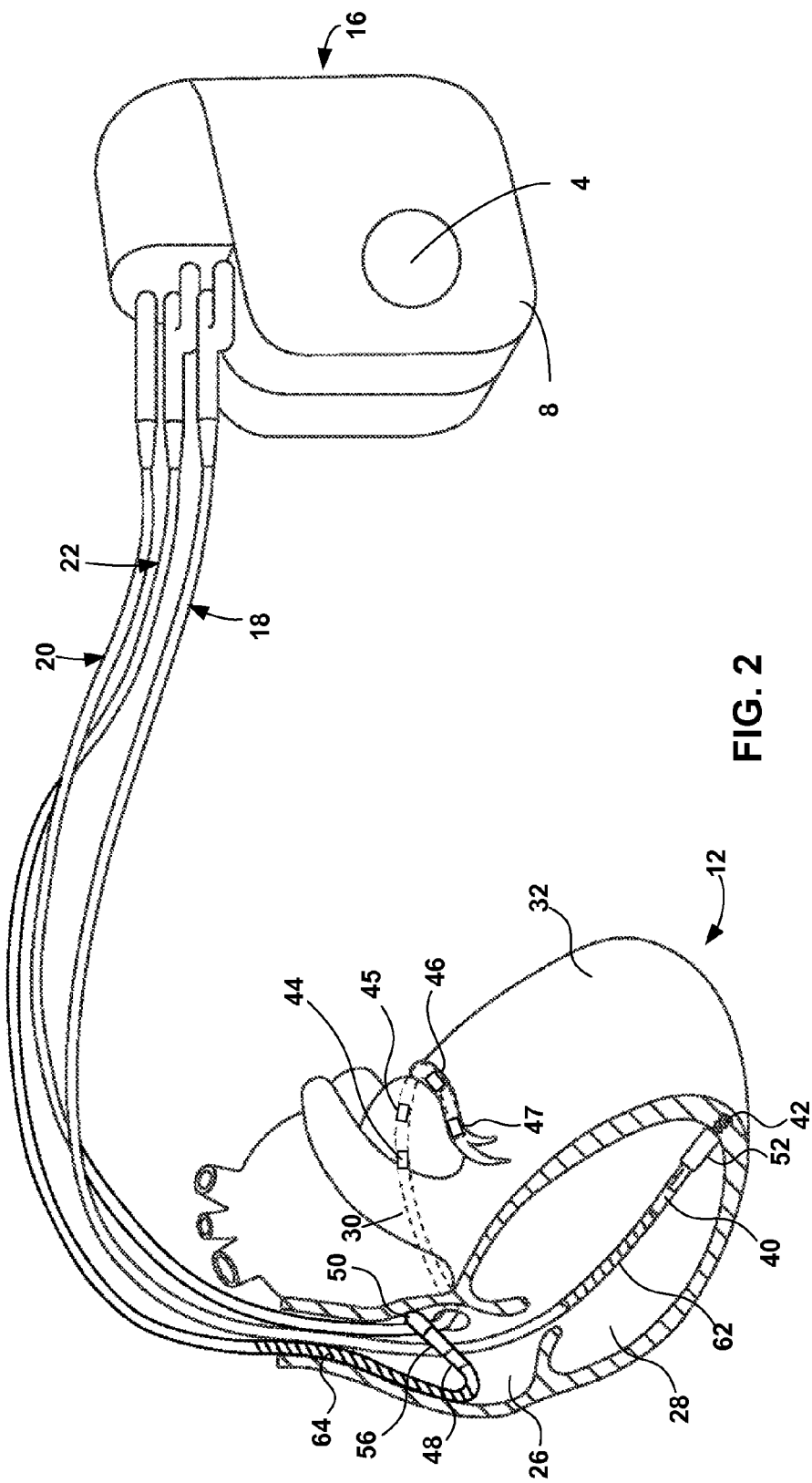
FIG. 2 is a conceptual diagram illustrating the IMD and leads of the system of FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. Leads 18 and 22 also include elongated electrodes 62 and 64, respectively, which may take the form of a coil. In some examples, each of electrodes 40, 42, 44-48, 50, 62, and 64 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a memory for storing the sensed electrical signals. Housing 8 may also enclose a telemetry module for communication between IMD 16 and programmer 24.

IMD 16 senses electrical signals attendant to the depolarization and repolarization of heart 12 via electrodes 4, 40, 42, 44-48, 50, 62, and 64. IMD 16 may sense such electrical signals via any bipolar combination of electrodes 40, 42, 44-48, 50, 62, and 64. Furthermore, any of the electrodes 40, 42, 44-48, 50, 62, and 64 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within heart 12.

Figure 3:
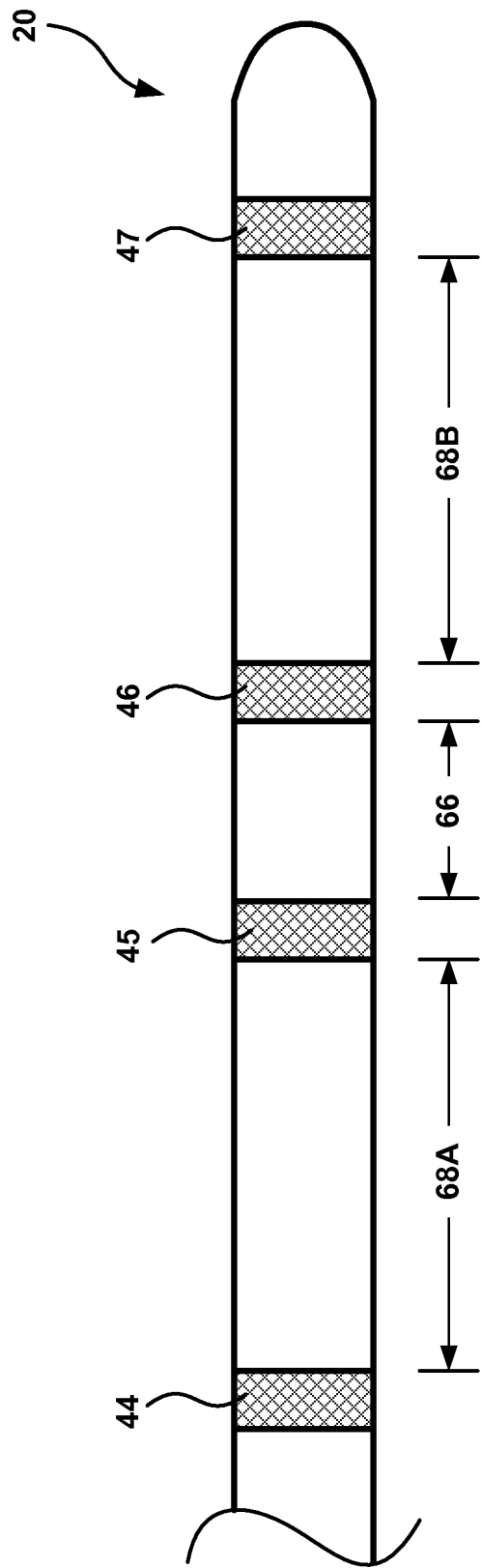
FIG. 3 is a conceptual diagram illustrating an example configuration of the left-ventricular lead of the system of FIG. 1.

FIG. 3 is a conceptual diagram illustrating an example configuration of LV lead 20. As illustrated in FIG. 3, LV lead 20 includes electrodes 44, 45, 46 and 47 located proximate to a distal end of LV lead 20. The distal end of LV lead 20, including electrodes 44, 45, 46 and 47, is placed in or near LV tissue, e.g., within the coronary sinus or a cardiac vein reachable via the coronary sinus.

As illustrated in FIG. 3, electrodes 44 and 45 are separated by an inter-electrode spacing 68A, electrodes 45 and 46 are separate by an inter-electrode spacing 66, and electrodes 46 and 47 are separated by an inter-electrode spacing 68B. Inter-electrode spacings refer to the distance, e.g., measured in a direction substantially parallel to a longitudinal axis of lead 20, from one electrode to another, e.g., center-to-center or edge-to-edge. In some example techniques for identifying abnormal cardiac substrate, electrodes 45 and 46 act as a bipolar electrode pair configured to sense a LV bipolar cardiac electrogram signal of tissue of the left ventricle 32 of heart 12 proximate electrodes 45 and 46. The bipolar electrode pair may be referred to as a short-spacing bipolar electrode pair due to the relatively smaller inter-electrode spacing 66 between electrodes 45 and 46, e.g., relative to inter-electrode spacings 68A and 68B. Inter-electrode spacing 66 may be, as examples, less than or equal to approximately five millimeters, less than or equal to approximately two millimeters, within a range from approximately 1.3 millimeters to approximately 5 millimeters, within a range between approximately 1.3 millimeters to approximately 1.5 millimeters, approximately 1.3 millimeters, or any range between any of 1.3 millimeters, 1.5 millimeters, two millimeters, or five millimeters.

Inter-electrode spacings 68A and 68B (collectively "inter-electrode spacings 68") are relatively larger than inter-electrode spacing 66. Inter-electrode spacings 68 may be the same as, or different than, each other. Inter-electrode spacings 68 may be, as examples, greater than or equal to approximately ten millimeters, greater than or equal to approximately twenty millimeters, greater than or equal to approximately twenty-one millimeters, or within any range between any of ten millimeters, twenty millimeters, and twenty-one millimeters. As will be described in greater detail below, delivering LV pacing via an electrode, e.g., electrode 44 or 47, that is at least a threshold distance from the bipolar electrode pair, e.g., electrodes 45 and 46, may facilitate identification of abnormal cardiac tissue according to the techniques of this disclosure. The threshold distance may be, as examples, approximately ten millimeters, approximately twenty millimeters, or approximately twenty-one millimeters. Accordingly, inter-electrode spacings 68 may facilitate delivery of LV pacing via electrode 44 or 47 at least the threshold distance from the bipolar pair of electrodes 45 and 46.

The arrangement of electrodes 44-47 and the inter-electrode spacings 66 and 68 illustrated in FIG. 3 are one example. Other example LV leads that may be included in a system according to this disclosure may include a different arrangement of electrodes and inter-electrode spacings. For example, on some LV leads that may be included in a system according to this disclosure, a most proximal pair of electrodes, e.g., electrodes 44 and 45, or a most distal pair of electrodes, e.g., electrode 46 and 47, may have an inter-electrode spacing 66 and act as a bipolar pair of electrodes configured to sense a LV bipolar cardiac electrogram signal of tissue of the left ventricle 32 of heart 12 proximate the bipolar electrode pair. Some LV leads may includes a plurality of electrodes having an inter-electrode spacing 66, and thus configured to act as a bipolar pair of electrodes configured to sense a LV bipolar cardiac electrogram signal of tissue of the left ventricle 32 of heart 12 proximate the bipolar electrode pair.

Figure 4:
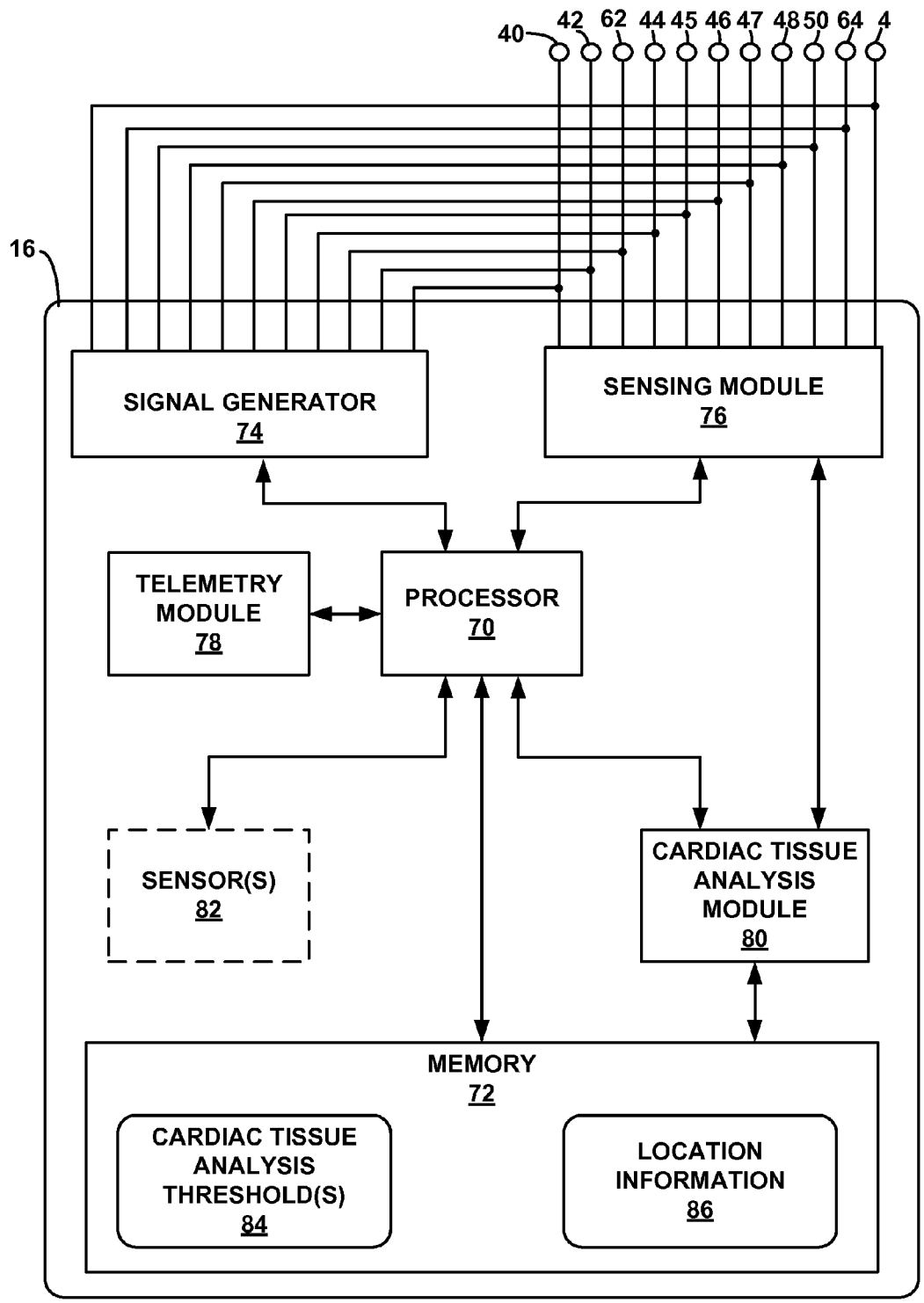
FIG. 4 block diagram illustrating an example configuration of an IMD for monitoring and treating cardiac events, which may be used to identify abnormal cardiac substrate according to the techniques of this disclosure.

FIG. 4 is a block diagram illustrating an example configuration of IMD 16, which may be used to identify abnormal cardiac substrate according to the techniques of this disclosure. In the illustrated example, IMD 16 includes a processor 70, memory 72, signal generator 74, sensing module 76, telemetry module 78, cardiac tissue analysis module 80, and one or more sensors 82. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters.

Signal generator 74 is configured to generate and deliver electrical stimulation therapy to patient 14. As shown in FIG. 4, signal generator 74 is electrically coupled to electrodes 4, 40, 42, 44-48, 50, 62, and 64, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44-48, 50, 62 and 64. In some examples, signal generator 74 delivers stimulation in the form of signals other than pulses such as sine waves, square waves, or other substantially continuous time signals.

In some examples, signal generator 74 includes a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44-48, 50, 62 and 64. In some examples, sensing module 76 also includes a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70 or cardiac tissue analysis module 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 and cardiac tissue analysis module 80 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase.

One or more sensors 82 may be optionally included in some examples of IMD 16. Sensor 82 may include one or more accelerometers in some examples. Sensors 82 may additionally or alternatively include other sensors such as a heart sounds sensor, a pressure sensor, a flow sensor, or an $O_2$ saturation sensor. In some examples, sensors 82 may detect respiration via one or more electrodes.

Processor 70 may use the information obtained from activity sensor 82 to determine activity level, posture, blood pressure, blood flow, blood oxygen level, or respiratory rate, as examples. In some examples, this information may be used by IMD 16 to aid in the classification of an abnormal heart rhythm. In some examples, this information may be used by IMD 16 or a user of programmer 24 to determine desired LV pacing locations and timings for delivery of CRT. For example, blood pressure or flow metrics may indicate the effectiveness LV pacing locations and timings in improving the performance of heart 12.

In some examples, sensors 82 are located outside of the housing 8 of IMD 16. Sensors 82 may be located on a lead that is coupled to IMD 16 or may be implemented in a remote sensor that wirelessly communicates with IMD 16 via telemetry module 78. In any case, sensors 82 are electrically or wirelessly coupled to circuitry contained within housing 8 of IMD 16.

In some examples, IMD 16 comprises a cardiac tissue analysis module 80, and the cardiac tissue analysis module and IMD 16 are configured to perform techniques for identifying abnormal cardiac substrate of left-ventricle 32, as described herein. According to some examples, sensing module 76 senses an LV bipolar electrogram signal via a bipolar pair of electrodes, e.g., electrodes 45 and 46, of LV lead 20. As discussed above, sensing module 76 may include a wide-band amplifier, and sensing module 76 may sense the LV bipolar electrogram signal with the wide-band sensing amplifier. Sensing module 76 senses the LV bipolar electrogram signal during LV pacing, e.g., at times when the heart is paced, and depolarizes in response to the pacing rather than intrinsic conduction. Under the control of processor 70, signal generator 74 delivers LV pacing to left ventricle 32 via one or more of the electrodes, e.g., electrode 44 or 47, of LV lead 20, or another implantable LV lead.

Sensing module 76, processor 70, and/or cardiac tissue analysis module 80 may digitize the LV bipolar electrogram signal. Cardiac tissue analysis module 80 is configured to determine an amplitude of a depolarization within the LV bipolar cardiac electrogram signal, the depolarization resulting from the delivery of cardiac pacing pulses to the left ventricle 32. The amplitude indicates whether the LV tissue proximate the bipolar electrode pair comprises abnormal cardiac substrate. In some examples, cardiac tissue analysis module 80 is configured to compare the amplitude of the depolarization to a threshold amplitude. As illustrated in FIG. 4, memory 72 may store one or more cardiac tissue analysis threshold amplitudes 84 accessible by cardiac tissue analysis module 80 to facilitate this comparison.

Cardiac tissue analysis module 80 is configured such that, if the amplitude of the depolarization is less than the threshold amplitude, cardiac tissue analysis module 80 provides an indication that the LV tissue proximate the bipolar electrode pair comprises abnormal cardiac substrate, e.g., scar substrate. In some examples, cardiac tissue analysis module is configured to, in response to determining the amplitude of the depolarization is greater than the threshold amplitude, provide an indication that the LV tissue proximate the bipolar electrode pair comprises normal cardiac substrate. In some examples, cardiac tissue analysis module 80 provides the result of the comparison of the determined amplitude to the threshold amplitude as the indication. Cardiac tissue analysis module 80 may provide the indication to telemetry module 78, e.g., via processor 70, which may provide the indication and/or other information based thereon to programmer 24 or another external computing device. The threshold depolarization amplitude, e.g., stored as a cardiac tissue analysis threshold 84 by memory 72, may be, as examples, less than approximately 1.5 millivolts, approximately 1.1 millivolts, approximately 1 millivolt, or within any range between or including any of approximately 5 millivolts, approximately 1.1 millivolts, and approximately 1 millivolt.

As illustrated in FIG. 4, memory 72 may also store location information 86. Location information 86 identifies locations of electrodes 44-47 of LV lead 20, e.g., the location of the bipolar electrode pair including electrodes 45 and 46. Location information 86 may identify different locations of the electrodes at different times, e.g., as the distal end of LV lead 20 is moved to different locations within the coronary sinus or cardiac veins. Cardiac tissue analysis module 80 may store contemporaneous indications of whether LV tissue proximate the bipolar pair of electrodes comprises abnormal (or normal) cardiac substrate with location information 86. Accordingly, cardiac tissue analysis module 80 and/or processor 70 may indicate the locations of abnormal (or normal) cardiac substrate via telemetry module 78. The indication of locations of abnormal (or normal) cardiac substrate may facilitate implantation of LV lead 20 to avoid abnormal cardiac substrate and/or procedures to modify LV tissue including abnormal cardiac substrate, such as ablation.

The locations of the electrodes may be determined using any known techniques, such as fluoroscopy or other imaging, or through measuring electrical potentials on the electrodes when exposed to an electrical field, e.g., generated by surface electrodes on patient 14. As examples, the locations of the electrodes may be determined using the LocaLisa® system commercially available from Medtronic, Inc., of Minneapolis, Minn., or the EnSite NavX® system commercially available from St. Jude Medical, Inc., of St. Paul, Minn. Processor 70 and/or cardiac tissue analysis module 80 may receive such electrode location information, e.g., from such systems, via telemetry module 78.

Although processor 70 and cardiac tissue analysis module 80 are illustrated as separate modules in FIG. 4, processor 70 and cardiac tissue analysis module 80 may be incorporated in a single processing unit in other examples. Cardiac tissue analysis module 80 may be a component of, or a software or firmware module executed by, processor 70.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., EGM signals, produced by sensing module 76. For example, processor 70 may transmit an LV bipolar cardiac electrogram signal to programmer 24 or another external computing device via telemetry module 78, e.g., to facilitate analysis of the signal by the external computing device to identify abnormal cardiac tissue according to the techniques of this disclosure. In some examples, telemetry module 78 transmits indications of abnormal cardiac substrate provided by episode classifier 80 to programmer 24 or another external computing device.

Processor 70 may also generate and store marker codes indicative of different cardiac or other physiological events detected by sensing module 76, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to respond in the same (or similar) manner to the therapy provided. Such information may be included as part of a marker channel with an EGM.

Figure 5:
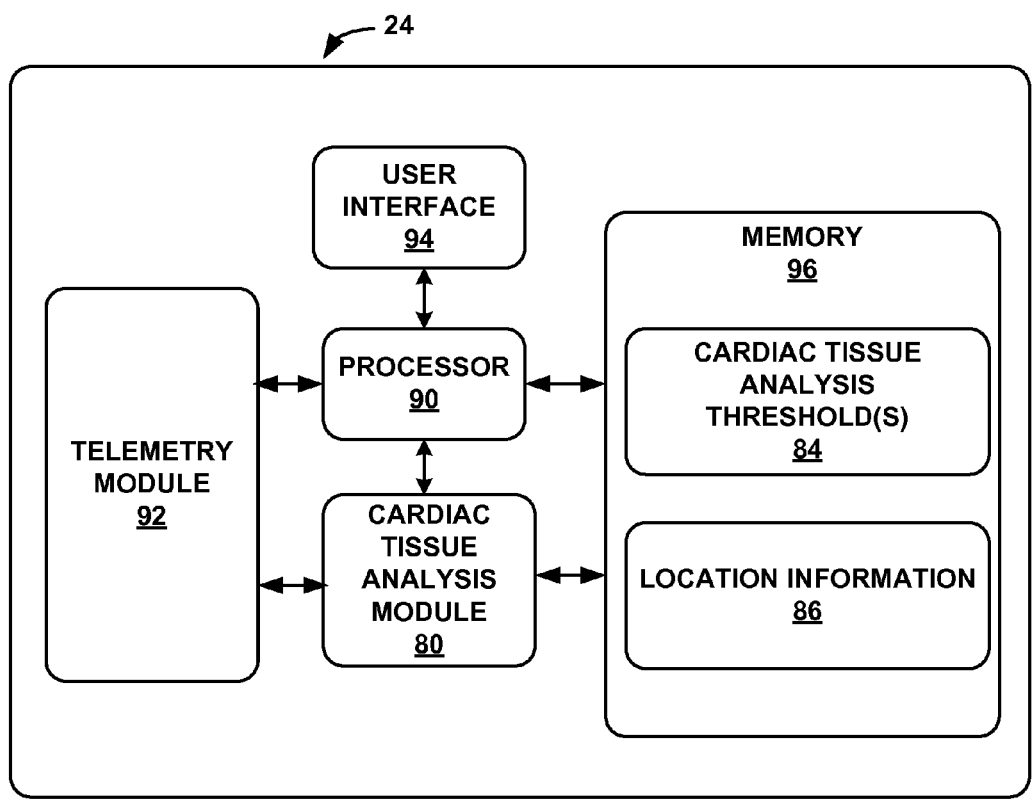
FIG. 5 is a block diagram illustrating an example configuration of an external programmer, which may be used with an IMD to identify abnormal cardiac substrate according to the techniques of this disclosure.

FIG. 5 is a block diagram illustrating an example configuration of external programmer 24, which may be used with an IMD to identify abnormal cardiac substrate according to the techniques of this disclosure. As illustrated in FIG. 5, programmer 24 may include a processor 90, a memory 96, a telemetry module 92, a user interface 94, and a cardiac tissue analysis module 80. Programmer 24 is an example of an external computing device that communicates with an IMD to perform the techniques for identifying abnormal cardiac substrate of this disclosure.

Processor 90 stores and retrieves information and instructions to and from memory 96. Processor 90 may include one or more microprocessors, microcontrollers, DSPs, ASICs, FPGAs, or other equivalent discrete or integrated logic circuitry, or any combination thereof. Accordingly, processor 90 may include any suitable structure, whether in hardware, software, firmware or any combination thereof, to perform the functions ascribed herein to processor 90.

Memory 92 may include program instructions that, when executed by processor 90 and/or cardiac tissue analysis module 80, cause the processor and/or cardiac tissue analysis module to perform any of the functions attributed to them herein. Memory 96 may also include instructions for operating user interface 94 and telemetry module 92. Memory 96 may include any volatile or nonvolatile memory such as RAM, ROM, EEPROM or flash memory. Memory 96 may also include a removable memory portion that may be used to provide memory updates or increases in memory capacities. A removable memory may also allow sensitive patient data to be removed before programmer 24 is used by, or for, a different patient.

Telemetry module 92 receives data from IMD 16, and may provide program instructions from processor 90 to IMD 16. In various examples, telemetry module 92 includes any of a variety of circuitry known to facilitate wireless, e.g., radio-frequency or inductive, communication with IMD 16. In some examples, processor 90 receives indications that LV tissue proximate a bipolar pair of electrodes (e.g., electrodes 45, 46) comprises abnormal cardiac substrate from IMD 16 via telemetry module 92. Processor 90 may present indications that LV tissue proximate the bipolar pair of electrodes comprises abnormal cardiac substrate to a user, e.g., a physician, surgeon, or other clinician, via user interface 94. Processor 90 may also present location information 86 of the electrodes (and thus of the abnormal cardiac substrate) to the user via user interface 94. As illustrated in FIG. 5, memory 96 may store the location information 86. Processor 90 may receive location information 86 from IMD 16, or from another system, as described above with respect to IMD 16 and FIG. 4. In some examples, programmer 24 incorporates such a system to locate implanted electrodes, or such a system incorporates programmer 24.

In other examples, as illustrated in FIG. 5, programmer 24 includes cardiac tissue analysis module 80, and the cardiac tissue analysis module and programmer 24 are configured to perform the techniques for identifying abnormal cardiac substrate substantially as described above with respect to IMD 16 and FIG. 4. In such examples, cardiac tissue analysis module 80 receives the LV bipolar cardiac electrogram signal, e.g., a digitized LV bipolar cardiac electrogram signal, from IMD 16 via telemetry module 92. Cardiac tissue analysis module 80 determines depolarization amplitudes within the LV bipolar cardiac electrogram signal. In some examples, cardiac tissue analysis module 80 compares the depolarization amplitudes to one or more threshold amplitudes, as described above with respect to FIG. 4. In such examples, memory 96 stores cardiac tissue analysis thresholds 84, which include the one or more threshold depolarization amplitudes. Based on the determined depolarization amplitudes, e.g., based on the comparison to the threshold depolarization amplitude, cardiac tissue analysis module 80 provides an indication of whether the LV tissue proximate the bipolar electrode pair comprises abnormal cardiac substrate, e.g., to a user via user interface 94.

User interface 94 includes a display (not shown), such as a LCD or LED display or other type of screen, to present any indications or information described herein for the techniques for identifying abnormal cardiac substrate according to this disclosure. In addition, user interface 94 may include an input mechanism to receive input from the user. The input mechanisms may include, for example, buttons, a keypad (e.g., an alphanumeric keypad), a peripheral pointing device, or another input mechanism that allows the user to navigate through user interfaces presented by processor 84 of programmer 24 and provide input. The input may include, for example, instructions to control IMD 16, programmer 24, and cardiac tissue analysis module 80 in the performance of the techniques for identifying abnormal cardiac substrate according to this disclosure. In some examples, the display (not shown) of programmer 24 may be a touch screen that allows the user to provide input directly to the user interface shown on the display. The user may use a stylus or a finger to provide input to the display. In other examples, user interface 94 additionally or alternatively includes audio circuitry for providing audible instructions or sounds to a user and/or receiving voice commands from the user.

Although processor 90 and cardiac tissue analysis module 80 are illustrated as separate modules in FIG. 5, processor 90 and cardiac tissue analysis module 80 may be incorporated in a single processing unit. Cardiac tissue analysis module 80 may be a component of or a module executed by processor 90.

In some examples, a system for identifying abnormal cardiac substrate of a left-ventricle during LV pacing includes any of a variety of networked external computing devices, such as servers, programmers, and client computing devices coupled via a network. Such systems may be implemented, in some aspects, with general network technology and functionality similar to that provide by the Medtronic CareLink® Network developed by Medtronic, Inc., of Minneapolis, Minn. In such examples, any one or more external computing devices of such a system may include a cardiac tissue analysis module, or may otherwise individually or collectively perform any of the techniques identifying abnormal cardiac substrate of a left-ventricle during LV pacing described herein.

Figure 6:
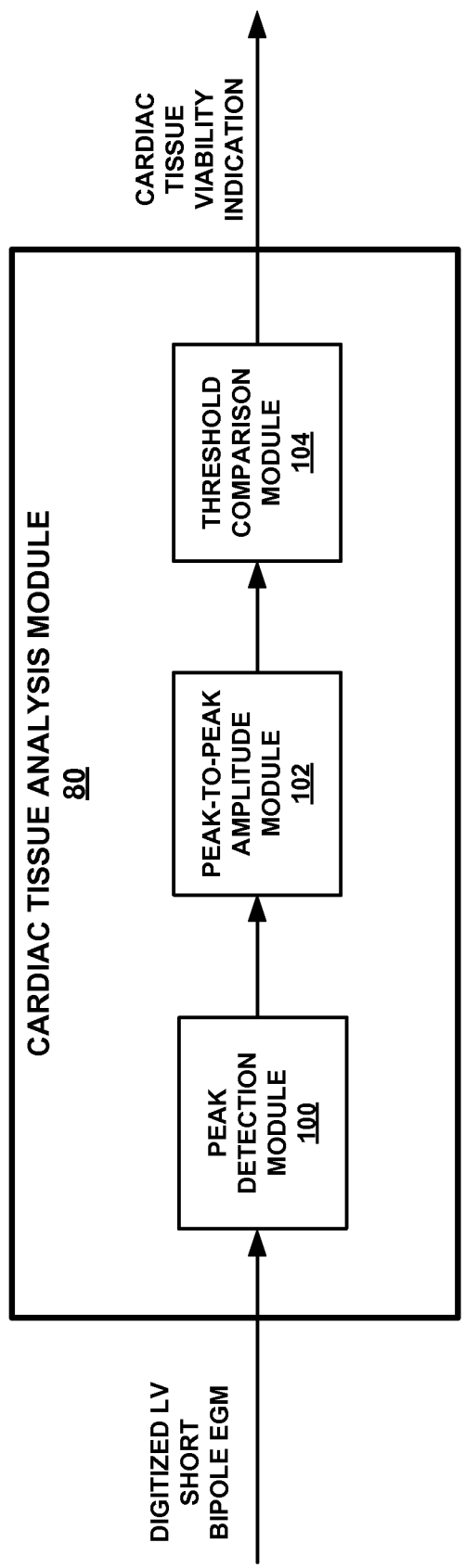
FIG. 6 is a block diagram illustrating an example cardiac tissue analysis module that may be used to identify abnormal cardiac substrate according to the techniques of this disclosure.

FIG. 6 is a block diagram illustrating an example configuration of cardiac tissue analysis module 80. In the illustrated example, cardiac tissue analysis module 80 includes a peak detection module 100, peak-to-peak amplitude module 102, and threshold comparison module 104. In some examples, cardiac tissue analysis module 80 includes other modules and provides other functionality not illustrated in or described with respect to FIG. 6.

As illustrated in FIG. 6, cardiac tissue analysis module 80 receives an LV bipolar cardiac electrogram signal, e.g., sensed by sensing module 76 of IMD 16. In some examples, LV bipolar cardiac electrogram signal is sensed via a short-spaced bipole. In some examples, the LV bipolar cardiac electrogram signal is digitized.

Peak detection module 100 identifies LV depolarizations, e.g., QRS complexes, within the LV bipolar cardiac electrogram signal. For each depolarization, peak detection module 100 identifies one or more peaks, e.g., negative and/or positive peaks, which may be associated with the Q-wave, R-wave, or S-wave of the QRS complex. In the illustrated example, peak detection module 100 identifies a positive peak and a negative peak for each depolarization. Peak detection module 100 may employ any technique to identify peaks, such as determining a derivative signal of the LV bipolar cardiac electrogram signal, and identifying zero-crossings with the derivative signal.

For each identified depolarization, peak-to-peak amplitude module 102 determines the peak-to-peak amplitude, e.g., peak-to-peak voltage, of the depolarization based on the amplitudes of the peaks identified by peak detection module 100. The peak-to-peak amplitude of the depolarization may be the difference between a positive peak and a negative identified by peak detection module 100. In other examples, the determined amplitude of a depolarization within the LV bipolar cardiac electrogram signal is not a peak-to-peak amplitude. In such examples, the determined amplitude of a depolarization within the LV bipolar cardiac electrogram signal may be a positive peak amplitude, negative peak amplitude, or the greatest positive or negative peak amplitude within the depolarization.

Threshold comparison module 104 compares the peak-to-peak (or other) amplitude of the depolarization to a threshold depolarization amplitude value 84. In some examples, threshold comparison module 104 compares the peak-to-peak (or other) amplitudes of a plurality of depolarizations, e.g., consecutive depolarizations, to a threshold depolarization amplitude value 84. In either case, threshold comparison module 104 provides an indication of cardiac tissue viability based on the comparison. In some examples, threshold comparison module 104 indicates that the LV tissue proximate the bipolar electrode pair comprises abnormal cardiac substrate, e.g., scar substrate, in response to determining that the peak-topeak amplitude is less than the threshold. In some examples, threshold comparison module 104 indicates that the LV tissue proximate the bipolar electrode pair comprises normal cardiac substrate in response to determining that the peak-to-peak amplitude is greater than the threshold.

Figure 7:
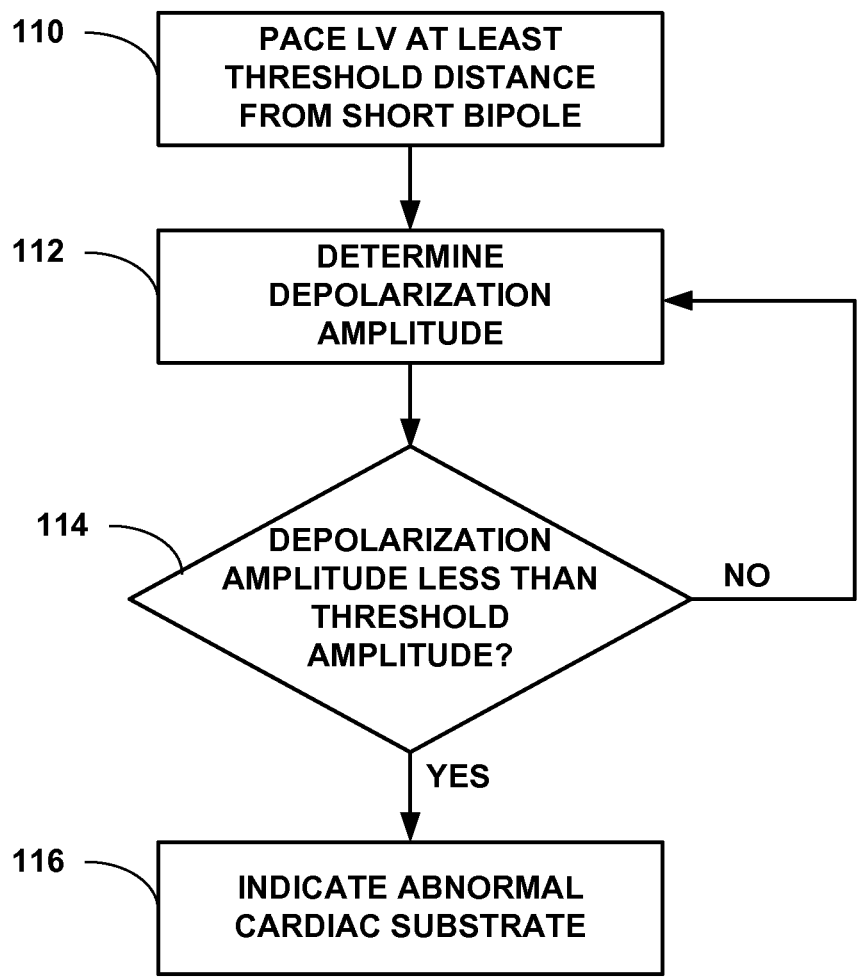
FIG. 7 is a flow diagram illustrating an example method of identifying abnormal cardiac substrate.

FIG. 7 is a flow diagram illustrating an example method of identifying abnormal cardiac substrate according to the techniques of this disclosure. According to the example method of FIG. 7, IMD 16 paces the left-ventricle 32 at least a threshold distance from a short bipole used to sense an LV cardiac electrogram signal of tissue proximate to the short bipole (110). As described herein, an LV lead 20 may include a bipolar pair of electrodes 45 and 46 that acts as the short bipole for sensing the LV cardiac electrogram signal. LV lead 20, or another LV lead, may include one or more electrodes for delivery of the LV pacing at least the threshold distance from a short bipole. The threshold distance from the LV pacing delivery electrode and the bipolar pair of electrodes may be, as examples, greater than or equal to approximately ten millimeters, greater than or equal to approximately twenty millimeters, greater than or equal to approximately twenty-one millimeters, or within any range between or including any of ten millimeters, twenty millimeters, and twenty-one millimeters.

A cardiac tissue analysis module 80 determines an amplitude, e.g., peak-to-peak voltage, of one or more LV-paced depolarizations within the LV cardiac electrogram signal (112). Cardiac tissue analysis module 80 determines whether the depolarization amplitude is less than a threshold depolarization amplitude (114). In response to determining that the depolarization amplitude is not less than, e.g., is greater than, the threshold, cardiac tissue analysis module 80 determines an amplitude of another one or more LV-paced depolarizations within the LV cardiac electrogram signal (112). In response to determining that the depolarization amplitude is less than the threshold, cardiac tissue analysis module 80 provides an indication that LV tissue proximate the bipolar pair of electrodes comprises abnormal cardiac substrate (116). The threshold depolarization amplitude, may be, as examples, less than approximately 1.5 millivolts, approximately 1.1 millivolts, approximately 1 millivolt, or within any range between or including any of approximately 5 millivolts, approximately 1.1 millivolts, and approximately 1 millivolt.

Figure 8:
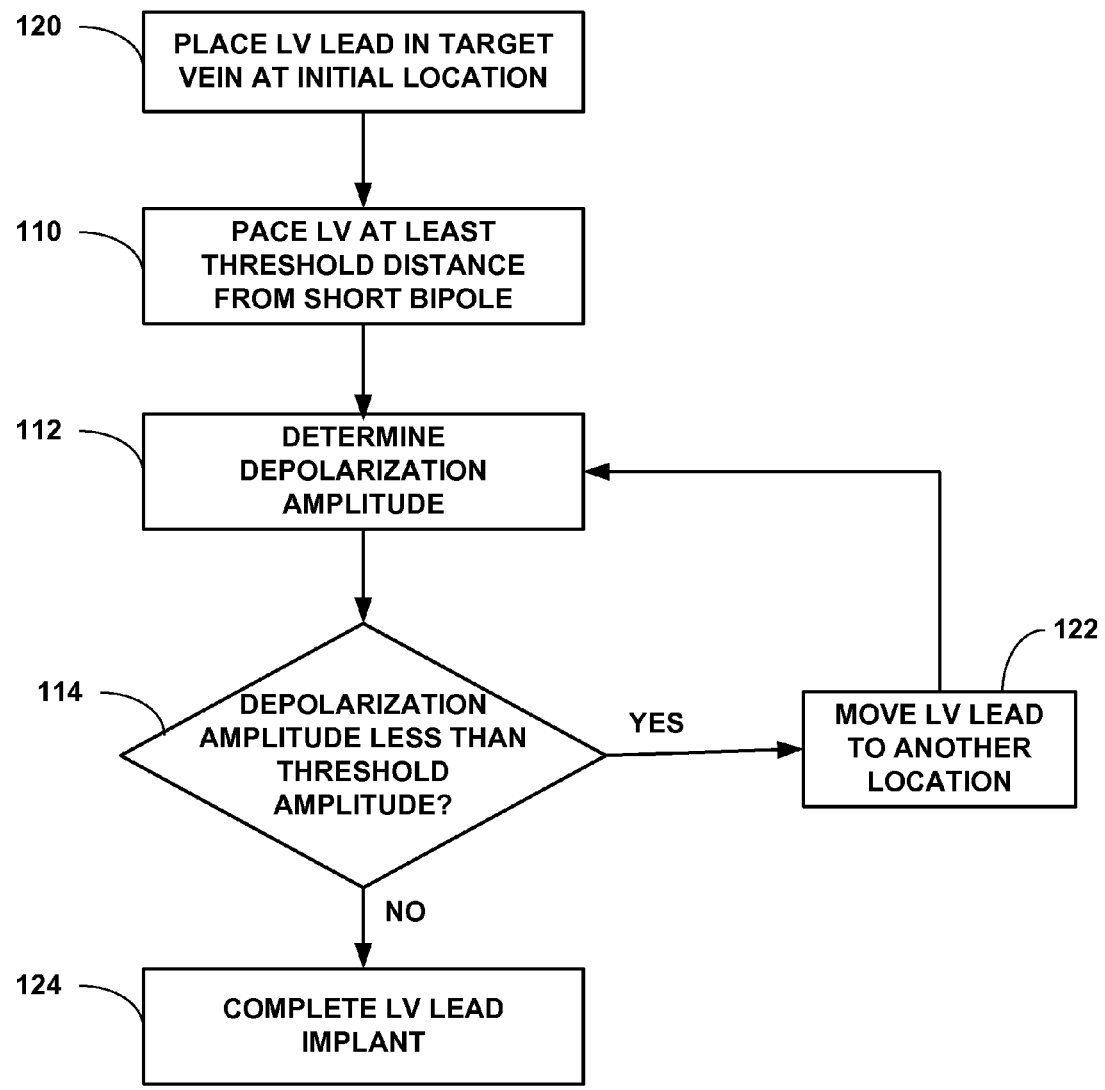
FIG. 8 is a flow diagram illustrating an example method of identifying abnormal cardiac substrate during left-ventricular lead implantation according to the techniques of this disclosure.

FIG. 8 is a flow diagram illustrating an example method of identifying abnormal cardiac substrate during LV lead implantation according to the techniques of this disclosure. According to the example method of FIG. 8, a clinician, or automated or semi-automated lead placement system, places an implantable LV lead, e.g., LV lead 20, at an initial location within a target cardiac vein (120). In some examples, the clinician or system places a distal end of the LV lead at the initial location.

IMD 16 paces the left-ventricle 32 at least the threshold distance from the bipolar pair of electrodes of the LV lead (110). Cardiac tissue analysis module 80 determines an amplitude of one or more LV-paced depolarizations within the LV cardiac electrogram signal (112), and determines whether the depolarization amplitude is less than a threshold depolarization amplitude (114). If the depolarization amplitude is less than the threshold, then cardiac tissue analysis module 80 may provide an indication that LV tissue proximate the bipolar pair of electrodes comprises abnormal cardiac substrate, and the clinician may move the LV lead to another location (122). If the depolarization amplitude is not less than, e.g., is greater than, the threshold, then cardiac tissue analysis module 80 may indicate that LV tissue proximate the bipolar pair of electrodes comprises normal cardiac substrate, and/or not indicate that the LV tissue proximate the bipolar pair of electrodes comprises abnormal cardiac substrate. In response to the indication of normal cardiac substrate, or lack of indication of abnormal cardiac substrate, the clinician may optionally test other LV implant locations, or may complete the LV lead implant (124).

In addition, or as an alternative to identifying abnormal cardiac substrate during LV lead implantation, the techniques of this disclosure may be used to identify abnormal cardiac substrate for mapping the locations of the abnormal cardiac substrate and/or performing a procedure to modify LV tissue proximate to the bipolar pair of electrodes, such as the abnormal cardiac substrate. In some examples, in response to an indication that the LV tissue comprises abnormal cardiac substrate, a clinician or device modifies the LV tissue proximate the bipolar electrode pair. Modifying the LV tissue proximate the bipolar electrode pair may include, for example, ablating the LV tissue proximate the bipolar electrode pair, such as tissue including and proximate the abnormal cardiac substrate.

An experimental study was performed in which a 5 French (Fr.) decapolar catheter was inserted into a lateral coronary vein, and quadripolar catheters were inserted into the right atrium and right ventricle in ten patients. Cardiac electrograms were obtained during sinus rhythm and pacing from all available bipoles. LV tissue with bipolar electrogram voltage ≤1.5 millivolts during sinus rhythm were considered scar. Receiver-operator characteristic curves were created to identify optimal cutoff voltage during pacing from the right ventricular apex and the left ventricle from bipoles located 9.6, 19.2, 28.8, and 38.4 millimeters from the sensing bipole.

A total of 9/50 bipolar LV electrograms had voltage <1.5 millivolts during normal sinus rhythm, and were classified as scar. LV pacing >1 centimeter (i.e., 10 millimeters) from the sensing bipole provided superior discrimination of scar from normal tissue (Positive Predictive Value (PPV)=1, Negative Predictive Value (NPV)=0.89) compared to LV pacing <1 cm from the sensing bipole (PPV=0.41, NPV=0.86) or RV pacing (PPV=0.63, NPV=0.90). In this study, bipolar voltage <1.1 millivolts provided optimal discrimination of scar and normal tissue during LV pacing >1 cm from the sensing bipole (Area Under the Curve (AUC) from receiver-operator characteristic curve analysis=0.731, P=0.0049). These experimental results indicate that LV scar can be identified accurately during LV pacing at least 1 centimeter (i.e., ten millimeters) from the sensing bipole.

The techniques described in this disclosure may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A system for identifying abnormal cardiac substrate, the system comprising:
   at least one implantable left-ventricular (LV) lead comprising a plurality of electrodes, wherein the plurality of electrodes includes at least one bipolar electrode pair configured to sense a LV bipolar cardiac electrogram signal of LV tissue proximate the bipolar electrode pair;
   a signal generator configured to deliver cardiac pacing pulses to a left ventricle via at least one electrode of the plurality of electrodes of the at least one LV lead,
      wherein the bipolar electrode pair does not include the at least one electrode of the plurality of electrodes via which the signal generator is configured to deliver cardiac pacing pulses to the left ventricle, and
      wherein a distance from the bipolar electrode pair to the at least one electrode of the plurality of electrodes via which the signal generator is configured to deliver cardiac pacing pulses to the left ventricle is greater than or equal to approximately ten millimeters; and
   a cardiac tissue analysis module configured to:
      determine an amplitude of a depolarization within the LV bipolar cardiac electrogram signal, the depolarization resulting from the delivery of cardiac pacing pulses to the left ventricle, wherein the amplitude indicates whether the LV tissue proximate the bipolar electrode pair comprises abnormal cardiac substrate; and
      provide an indication of whether the LV tissue proximate the bipolar electrode pair comprises abnormal cardiac substrate based on the amplitude.

2. The system of claim 1, wherein the bipolar pair of electrodes comprises an inter-electrode spacing that is at least one of: less than or equal to approximately five millimeters, less than or equal to approximately two millimeters, or approximately 1.3 millimeters.

3. The system of claim 1, wherein a distance from the bipolar electrode pair to the at least one electrode of the plurality of electrodes via which the signal generator is configured to deliver cardiac pacing pulses to the left ventricle is greater than or equal to approximately twenty millimeters.

4. The system of claim 1, wherein a distance from the bipolar electrode pair to the at least one electrode of the plurality of electrodes via which the signal generator is configured to deliver cardiac pacing pulses to the left ventricle is approximately twenty-one millimeters.

5. The system of claim 1, wherein the cardiac tissue analysis module is further configured to:
   compare the amplitude of the depolarization to a threshold amplitude; and
   in response to determining that the amplitude of the depolarization is less than the threshold amplitude, provide an indication that the LV tissue proximate the bipolar electrode pair comprises abnormal cardiac substrate.

6. The system of claim 5, wherein the threshold amplitude is less than 1.5 millivolts.

7. The system of claim 5, wherein the threshold amplitude is approximately 1.1 millivolts.

8. The system of claim 5, wherein the threshold amplitude is approximately 1 millivolt.

9. The system of claim 1, wherein the amplitude indicates whether the LV tissue proximate the bipolar electrode pair comprises scar substrate, and the cardiac tissue analysis module is configured to provide an indication of whether the LV tissue proximate the bipolar electrode pair comprises scar substrate based on the amplitude.

10. The system of claim 1, wherein the cardiac tissue analysis module is configured to determine a peak-to-peak amplitude of the depolarization, wherein the peak-to-peak amplitude indicates whether the LV tissue proximate the bipolar electrode pair comprises abnormal cardiac substrate.

11. The system of claim 1, further comprising a user interface, wherein the cardiac tissue analysis module is configured to provide the indication of whether the LV tissue proximate the bipolar electrode pair comprises abnormal cardiac substrate to a user via the user interface.

12. The system of claim 1, further comprising:
   an implantable medical device coupled to the at least one implantable LV lead, wherein the implantable medical device comprises the signal generator; and
   an external computing device configured to communicate with the implantable medical device, wherein the external computing device comprises a user interface, wherein the cardiac tissue analysis module is configured to provide the indication of whether the LV tissue proximate the bipolar electrode pair comprises abnormal cardiac substrate to a user via the user interface,
   wherein at least one of the implantable medical device and the external computing device comprises the cardiac tissue analysis module.

13. The system of claim 1, further comprising an implantable medical device configured to be coupled to the at least one implantable LV lead, wherein the implantable medical device is configured to deliver cardiac resynchronization therapy via at least one electrode of the plurality of electrodes of the LV lead.

14. A method for identifying abnormal cardiac substrate, the method comprising:
   sensing, by a bipolar electrode pair, a left-ventricular (LV) bipolar cardiac electrogram signal of LV tissue proximate the bipolar electrode pair, wherein at least one implanted LV lead comprises a plurality of electrodes, and the plurality of electrodes includes the bipolar electrode pair;
   delivering, by a signal generator, cardiac pacing pulses to a left ventricle via at least one electrode of the plurality of electrodes of the at least one LV lead,
      wherein the bipolar electrode pair does not include the at least one electrode of the plurality of electrodes via which the signal generator is configured to deliver cardiac pacing pulses to the left ventricle, and wherein a distance from the bipolar electrode pair to the at least one electrode of the plurality of electrodes via which the signal generator is configured to deliver cardiac pacing pulses to the left ventricle is greater than or equal to approximately ten millimeters;

determining, by a cardiac tissue analysis module, an amplitude of a depolarization within the LV bipolar cardiac electrogram signal, the depolarization resulting from the delivery of cardiac pacing pulses to the left ventricle, wherein the amplitude indicates whether the LV tissue proximate the bipolar electrode pair comprises abnormal cardiac substrate; and providing, by the cardiac tissue analysis module, an indication of whether the LV tissue proximate the bipolar electrode pair comprises abnormal cardiac substrate based on the amplitude.

15. The method of claim 14, wherein the bipolar pair of electrodes comprises an inter-electrode spacing that is at least one of: less than or equal to approximately five millimeters, less than or equal to approximately two millimeters, or approximately 1.3 millimeters.

16. The method of claim 14, wherein a distance from the bipolar electrode pair to the at least one electrode of the plurality of electrodes via the cardiac pacing pulses are delivered to the left ventricle is at least one of: greater than or equal to approximately twenty millimeters; or approximately twenty-one millimeters.

17. The method of claim 14, further comprising comparing the amplitude of the depolarization to a threshold amplitude, wherein providing the indication of whether the LV tissue proximate the bipolar electrode pair comprises abnormal cardiac substrate based on the amplitude comprises, in response to determining that the amplitude of the depolarization is less than the threshold amplitude, providing an indication that the LV tissue proximate the bipolar electrode pair comprises abnormal cardiac substrate.

18. The method of claim 17, wherein the threshold amplitude is at least one of: less than 1.5 millivolts; approximately 1.1 millivolts; or approximately 1 millivolt.

19. The method of claim 14, wherein the amplitude indicates whether the LV tissue proximate the bipolar electrode pair comprises scar substrate, and wherein providing the indication of whether the LV tissue proximate the bipolar electrode pair comprises abnormal cardiac substrate based on the amplitude comprises providing an indication of whether the LV tissue proximate the bipolar electrode pair comprises scar substrate based on the amplitude.

20. The method of claim 14, wherein providing the indication of whether the LV tissue proximate the bipolar electrode pair comprises abnormal cardiac substrate based on the amplitude comprises providing the indication to a user via a user interface.

21. The method of claim 14, wherein providing the indication of whether the LV tissue proximate the bipolar electrode pair comprises abnormal cardiac substrate comprises providing an indication that the LV tissue comprises abnormal cardiac substrate, the method further comprising moving the LV lead to a different implanted location in response to the indication that the LV tissue comprises abnormal cardiac substrate.

22. The method of claim 14, further comprising delivering cardiac resynchronization therapy via at least one electrode of the plurality of electrodes of the LV lead.

23. The method of claim 16, wherein providing the indication of whether the LV tissue proximate the bipolar electrode pair comprises abnormal cardiac substrate comprises providing an indication that the LV tissue comprises abnormal cardiac substrate, the method further comprising modifying the LV tissue proximate the bipolar electrode pair in response to the indication that the LV tissue comprises abnormal cardiac substrate.

24. The method of claim 23, wherein modifying the LV tissue comprises ablating the LV tissue.

25. A system for identifying abnormal cardiac substrate, the system comprising:

means for sensing, via a bipolar electrode pair, a left-ventricular (LV) bipolar cardiac electrogram signal of LV tissue proximate the bipolar electrode pair, wherein at least one implantable LV lead comprises a plurality of electrodes, and the plurality of electrodes includes the bipolar electrode pair;

means for delivering cardiac pacing pulses to a left ventricle via at least one electrode of the plurality of electrodes of the at least one LV lead,
wherein the bipolar electrode pair does not include the at least one electrode of the plurality of electrodes via which the signal generator is configured to deliver cardiac pacing to the left ventricle, and
wherein a distance from the bipolar electrode pair to the at least one electrode of the plurality of electrodes via which the signal generator is configured to deliver cardiac pacing pulses to the left ventricle is greater than or equal to approximately ten millimeters;

means for determining an amplitude of a depolarization within the LV bipolar cardiac electrogram signal, the depolarization resulting from the delivery of cardiac pacing pulses to the left ventricle, wherein the amplitude indicates whether the LV tissue proximate the bipolar electrode pair comprises abnormal cardiac substrate; and means for providing an indication of whether the LV tissue proximate the bipolar electrode pair comprises abnormal cardiac substrate based on the amplitude.

26. A non-transitory computer-readable storage medium comprising instructions that, when executed by at least one processor, cause the at least one processor to:

receive, via a bipolar electrode pair, a left-ventricular (LV) bipolar cardiac electrogram signal of LV tissue proximate the bipolar electrode pair, wherein at least one implantable LV lead comprises a plurality of electrodes, and the plurality of electrodes includes the bipolar electrode pair;

determine an amplitude of a depolarization within the LV bipolar cardiac electrogram signal, the depolarization resulting from the delivery of cardiac pacing pulses to a left ventricle via at least one electrode of the plurality of electrodes of the at least one LV lead, wherein the bipolar electrode pair does not include the at least one electrode of the plurality of electrodes via which the signal generator is configured to deliver cardiac pacing pulses to the left ventricle, wherein a distance from the bipolar electrode pair to the at least one electrode of the plurality of electrodes via which the signal generator is configured to deliver cardiac pacing pulses to the left ventricle is greater than or equal to approximately ten millimeters, and wherein the amplitude indicates whether the LV tissue proximate the bipolar electrode pair comprises abnormal cardiac substrate; and provide an indication of whether the LV tissue proximate the bipolar electrode pair comprises abnormal cardiac substrate based on the amplitude.

27. A system for identifying abnormal cardiac substrate, the system comprising:

at least one implantable left-ventricular (LV) lead comprising a plurality of electrodes, wherein the plurality of electrodes includes at least one bipolar electrode pair configured to sense a LV bipolar cardiac electrogram signal of LV tissue proximate the bipolar electrode pair, wherein the bipolar pair of electrodes comprises an inter-electrode spacing that is less than or equal to approximately two millimeters;

a signal generator configured to deliver cardiac pacing pulses to a left ventricle via at least one electrode of the plurality of electrodes of the at least one LV lead, wherein the bipolar electrode pair does not include the at least one electrode of the plurality of electrodes via which the signal generator is configured to deliver cardiac pacing pulses to the left ventricle, and a distance from the bipolar electrode pair to the at least one electrode of the plurality of electrodes via which the signal generator is configured to deliver cardiac pacing pulses to the left ventricle is greater than or equal to approximately ten millimeters;

a cardiac tissue analysis module configured to determine whether an amplitude of a depolarization within the LV bipolar cardiac electrogram signal resulting from the delivery of cardiac pacing pulses to the left ventricle is less than a threshold; and a user interface configured to indicate that the LV tissue proximate the bipolar electrode pair comprises scar substrate in response to the amplitude being less than the threshold.

* * * * *